United States Patent
Mitelberg et al.

(10) Patent No.: US 10,238,411 B2
(45) Date of Patent: Mar. 26, 2019

(54) FLEXIBLE ENDOSCOPIC TORQUEABLE DEVICES

(71) Applicant: Apollo Endosurgery, Inc., Austin, TX (US)

(72) Inventors: Vladimir Mitelberg, Austin, TX (US); Donald K. Jones, Dripping Springs, TX (US)

(73) Assignee: Apollo Endosurgery US, Inc., Austin, TX (US)

( * ) Notice: Subject to any disclaimer, the term of this patent is extended or adjusted under 35 U.S.C. 154(b) by 404 days.

(21) Appl. No.: 14/785,615

(22) PCT Filed: Apr. 18, 2014

(86) PCT No.: PCT/US2014/034712
§ 371 (c)(1),
(2) Date: Oct. 19, 2015

(87) PCT Pub. No.: WO2014/172676
PCT Pub. Date: Oct. 23, 2014

(65) Prior Publication Data
US 2016/0066947 A1    Mar. 10, 2016

Related U.S. Application Data

(60) Provisional application No. 61/814,201, filed on Apr. 20, 2013.

(51) Int. Cl.
*A61B 17/3201* (2006.01)
*A61B 17/32* (2006.01)
(Continued)

(52) U.S. Cl.
CPC ...... *A61B 17/320016* (2013.01); *A61B 1/018* (2013.01); *A61B 17/29* (2013.01);
(Continued)

(58) Field of Classification Search
CPC ........ A61B 17/320016; A61B 17/3201; A61B 17/3205; A61B 2017/00323; A61B 2017/0034
See application file for complete search history.

(56) References Cited

U.S. PATENT DOCUMENTS 5,439,478 A * 8/1995 Palmer ............... A61B 1/00087
                                                   600/564
5,496,347 A * 3/1996 Hashiguchi ............ A61B 17/29
                                                   600/564
(Continued)

FOREIGN PATENT DOCUMENTS

EP        0572131       12/1993

OTHER PUBLICATIONS

International Search Report and Written Opinion for PCT/US14/34712 dated Sep. 8, 2014 in 28 pages.

*Primary Examiner* — Ryan J. Severson
(74) *Attorney, Agent, or Firm* — Donald K. Jones

(57) ABSTRACT

An elongate flexible endoscopic surgical scissor instrument includes an actuating means at the proximal end and a blade assembly that includes pair of pivotable scissor blades at the distal end. The actuating means is adapted to place the scissor blades in an opened or closed configuration. The scissors include a torque-transmitting shaft assembly that couples the proximal end of instrument to the blade assembly positioned at the distal end. Rotation of the torque transmitting shaft assembly at the proximal end causes the distally-located blade assembly to similarly rotate in both the open and closed configurations, which can provide precise targeting.

18 Claims, 7 Drawing Sheets

(51) Int. Cl.
*A61B 17/29* (2006.01)
*A61B 1/018* (2006.01)
*A61B 17/00* (2006.01)

(52) U.S. Cl.
CPC .. *A61B 17/3201* (2013.01); *A61B 2017/0034* (2013.01); *A61B 2017/00323* (2013.01); *A61B 2017/2929* (2013.01)

(56) References Cited

U.S. PATENT DOCUMENTS

| | | | | |
|---|---|---|---|---|
| 5,499,992 | A * | 3/1996 | Meade | A61B 17/29 606/170 |
| 5,540,685 | A | 7/1996 | Parins et al. | |
| 5,582,614 | A | 12/1996 | Klieman et al. | |
| 5,797,958 | A | 8/1998 | Yoon | |
| 5,893,874 | A * | 4/1999 | Bourque | A61B 17/29 606/170 |
| 6,027,522 | A * | 2/2000 | Palmer | A61B 10/06 606/205 |
| 6,773,434 | B2 * | 8/2004 | Ciarrocca | A61B 18/1445 606/170 |
| 7,494,501 | B2 * | 2/2009 | Ahlberg | A61B 17/282 606/207 |
| 7,569,062 | B1 | 8/2009 | Kuehn et al. | |
| 7,578,832 | B2 * | 8/2009 | Johnson | A61B 17/1608 606/174 |
| 8,037,591 | B2 | 10/2011 | Spivey et al. | |
| 8,353,487 | B2 | 1/2013 | Trusty et al. | |
| 8,394,095 | B2 | 3/2013 | Garrison et al. | |
| 9,277,932 | B2 * | 3/2016 | Slater | A61B 17/320016 |
| 2005/0101991 | A1 * | 5/2005 | Ahlberg | A61B 17/282 606/205 |
| 2005/0192598 | A1 * | 9/2005 | Johnson | A61B 17/1608 606/148 |
| 2007/0244515 | A1 * | 10/2007 | Fanous | A61B 17/295 606/205 |
| 2010/0298852 | A1 | 11/2010 | Slater | |
| 2013/0090526 | A1 | 4/2013 | Suzuki et al. | |
| 2016/0066947 | A1 * | 3/2016 | Mitelberg | A61B 1/018 606/170 |

\* cited by examiner

FLEXIBLE ENDOSCOPIC TORQUEABLE DEVICES

INCORPORATION BY REFERENCE TO ANY PRIORITY APPLICATIONS

This application is a United States national stage application under 35 U.S.C. § 371 of PCT Application No. PCT/US2014/034712 designating the United States, filed Apr. 18, 2014, titled "FLEXIBLE ENDOSCOPIC TORQUEABLE DEVICES," which claims priority benefit under 35 U.S.C. § 119(e) of U.S. Provisional Patent Application No. 61/814,201, filed Apr. 20, 2013, titled "FLEXIBLE ENDOSCOPIC TORQUEABLE DEVICES," which is hereby incorporated by reference in its entirety.

BACKGROUND

Field

The present disclosure relates generally to endoscopic surgical instruments. In particular, the present disclosure relates to endoscopic instruments suitable for passage through the working channel of an endoscope and, more particularly, to means for increasing the transmission torque applied to an end effector positioned at the distal end of an endoscopic instrument such as a pair of scissor blades.

Description of the Related Art

Endoscopic surgical scissor instruments are primarily used in laparoscopic surgical procedures for cutting tissue, suture and other prosthetic materials. There exists many different varieties of endoscopic scissor instruments for laparoscopic use that incorporate novel blade technology, cautery capability (both mono-polar and bi-polar), articulating ends and numerous other modifications.

Generally, these instruments have an elongate rigid tubular shaft, typically 30 cm to 60 cm in length, with a handle positioned at the proximal end of the shaft and a pair of actuatable scissor blades positioned at the distal end of the shaft. Actuation means, typically a pull wire, generally couple the handle to the scissor blades and is positioned with the rigid shaft to cause the scissor blades to open and close when the handle is manipulated. With the general rigid construction of these surgical scissor instruments, the physician has the ability to precisely orient the scissor blades relative to the intended target and cut with ease.

BRIEF SUMMARY

The present disclosure is directed towards a flexible endoscopic scissor instrument for use through the working channel of a flexible endoscope that has proximally located handle assembly coupled to an elongate flexible hollow torque transmitting shaft member and a scissor blade assembly fixedly positioned at the shaft distal end. An elongate actuation member having proximal and distal ends is slidably positioned within the lumen of the torque transmitting shaft member. The proximal end of the actuation member is coupled to the handle assembly whereas the distal end is coupled to the scissor blade assembly such that when the handle member is operated, the actuation member is moved longitudinally relative to the torque transmitting shaft member thereby causing the scissor blades to move between open and closed configurations. The scissor blade assembly is preferably welded to the torque transmitting shaft member in a fixed relationship such that rotation of the proximal end of the shaft member causes the distal end of the shaft member to rotate accordingly, which can provide precise orientation control of the scissors blades relative to an intended target.

In accordance with an embodiment of the present disclosure, there is provided an elongate hollow torque transmitting shaft that takes the form of an elongate hollow multi-wire stranded cable having proximal and distal ends. The hollow cable includes a helically wound coil having proximal and distal ends which is coaxially disposed within the cable lumen. The hollow cable and the helical coil have lengths that are generally equivalent and make up essentially the entire length of the shaft. The shaft lengths may generally range from about 100 cm to about 350 cm. The hollow cable is secured to the coil in at least two locations along the length of the shaft, preferably at the proximal and distal ends and preferably by laser welding. Other means for securing the cable to the coil may be suitable such as resistance welding, soldering, crimping and adhesives or glues.

In accordance with another embodiment of the present disclosure, there is provided an elongate hollow torque transmitting shaft having proximal and distal ends including a helical coil generally extending the entire length of the shaft and a hollow multi-wire cable coaxially disposed about the helical coil and generally extending from the proximal end of the shaft to a position proximal to the distal end of the shaft. Preferably the distance from the distal end of the shaft to the distal end of the hollow cable is not more than about 60 cm and more preferably not more than about 45 cm. The proximal and distal end of the hollow cable is secured to the coil preferably through welding. Additionally, intermediate locations between the proximal and distal ends of the cable may also be secured to the coil.

Certain aspects of the disclosure are directed toward a flexible endoscopic surgical instrument. The surgical instrument can include an elongate, flexible shaft member having a proximal portion, a distal portion, and a lumen extending therethrough. The shaft member can be configured for delivery through a working channel of an endoscope. The shaft member can include an elongate cable member having a proximal portion and a distal portion, and an elongate coil member having a proximal portion and a distal portion. The cable member and the coil member can be in coaxial arrangement. The surgical instrument can include an elongate actuation member having a proximal portion and a distal portion. The actuation member can be slidably positioned in the shaft member. The surgical instrument can include a handle member having a body portion and a slidable portion. The body portion can be coupled to the proximal portion of the shaft member in a longitudinally fixed configuration. The slidable portion can be coupled to the proximal portion of the actuation member. An end effector can be coupled to the distal portion of the actuation member such that longitudinal movement of the actuation member actuates the end effector. Rotation of the proximal portion of the shaft member can be configured to rotate the end effector.

In any of the above-mentioned embodiments, a diameter of the shaft member can be less than or equal to about 3.2 mm.

In any of the above-mentioned embodiments, the cable member can be secured to the coil member by a number of welds. In certain embodiments, the number of welds is two welds. The welds can be longitudinally spaced apart along a length of the shaft (e.g., a first weld at a distal portion of the shaft and a second weld at a proximal portion of the shaft). In certain embodiments, the welds can be circumferential welds.

In any of the above-mentioned embodiments, the distal portion of the coil member can extend distal to the distal end of the cable member.

In any of the above-mentioned embodiments, the elongate coil member can be positioned in the elongate cable member.

In any of the above-mentioned embodiments, there can be an actuation member that takes the form of an elongate resilient wire. Suitable materials for the wire include stainless steels, nitinol and other generally biocompatible metals, alloys and materials including plastics and composites with low percentages of elongation.

In accordance with still yet another aspect of the present disclosure, there is provided an actuation member that takes the form of an elongate resilient multifilament cable. Suitable materials for the cable include stainless steels, nitinol and other generally biocompatible metals, alloys and materials including plastics and composites with low percentages of elongation.

Certain aspects of the disclosure are directed toward a method of manufacturing a flexible endoscopic surgical instrument having any of the features described herein. The method can include coaxially positioning an elongate coil member and a cable member to form a shaft member. The method can include welding the elongate coil member to the cable member. In certain aspects, the welding step can include forming two longitudinally spaced apart welds (e.g., a first weld at a distal portion of the shaft member and a second weld at a proximal portion of the shaft member). In certain aspects, the welding step can include forming at least one circumferential weld (e.g., two welds, three welds, or more). The method can include slidably positioning an actuation member within the shaft member. The method can include connecting an end effector to a distal portion of the actuation member such that longitudinal movement of the actuation member actuates the end effector. In certain aspects, rotation of the proximal portion of the shaft member can be configured to rotate the end effector. The method can include securing a body portion of a handle member to a proximal portion of the shaft member and securing a slidable portion of the handle member to a proximal portion of the actuation member.

Certain aspects of the disclosure are directed toward a method of using a flexible endoscopic surgical instrument including any of the features described herein. For example, the surgical instrument can include an elongate, flexible shaft member having a proximal portion, a distal portion, and a lumen extending through the shaft member. The shaft member can include an elongate cable member having a proximal portion and a distal portion, and an elongate coil member having a proximal portion and a distal portion. The cable member and the coil member can be in coaxial arrangement. The surgical instrument can include an elongate actuation member slidably positioned within the shaft member. The method can include inserting the surgical instrument through a working channel of an endoscope. In certain aspects, the method can include longitudinally moving the actuation member to actuate an end effector. In certain aspects, the method can include rotating a proximal portion of the shaft member to rotate the end effector.

These aspects of the disclosure and the advantages thereof will be more clearly understood from the following description and drawings of embodiments of the present disclosure.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No individual aspects of this disclosure are essential or indispensable.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

DETAILED DESCRIPTION

As the physician community moves to perform more minimally invasive procedures by using flexible endoscopes positioned through a natural orifice, there is a need to have flexible endoscopic surgical instruments that perform comparably to their laparoscopic brethren. In the case of endoscopic scissors, applying the aforementioned simple construction configurations of rigid endoscopic scissors to a flexible platform, having lengths of over 300 cm, generally yields instruments with poor performance characteristics.

Figure 1:
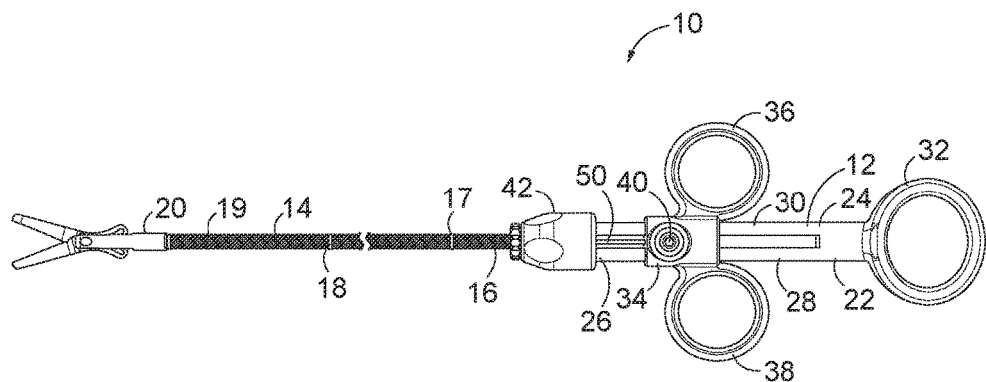
FIG. 1 is a view of a flexible endoscopic scissor instrument with the scissor blades in an open configuration according to an embodiment of the present disclosure.

Referring now to FIG. 1, there is shown a flexible endoscopic scissor instrument 10 for use in endoscopic surgical procedures and particularly suited for use through the working channel of a flexible endoscope positioned within the body though a natural orifice. Since the flexible endoscopic scissor instrument is suited for delivery through the working channel of a flexible endoscope it also suited for use with other flexible cannulas or passageways and as such, the term "endoscopic" should be construed to include arthroscopic, laparoscopic, robotic, etc. In some scenarios, the working channel can have a diameter of less than or equal to about 3.2 mm. Depending upon the length of the instrument, it will be adaptable to a variety of endoscopic procedures and will also be suitable for open surgical procedures.

Figure 2:
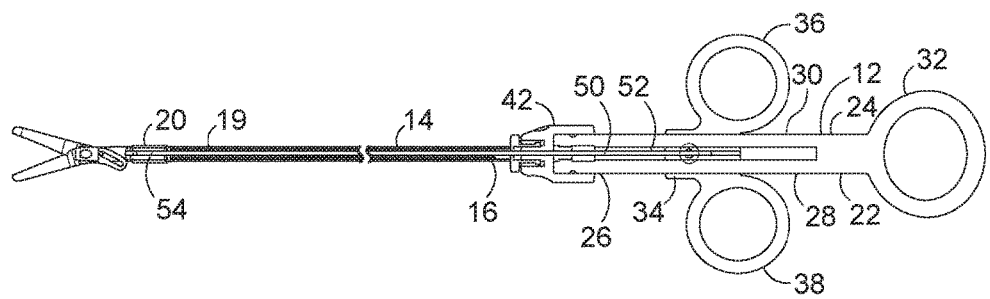
FIG. 2 is a partially sectioned view of the flexible endoscopic scissor instrument shown in FIG. 1.

As illustrated in FIG. 1, scissor instrument 10 includes a handle assembly 12 at the proximal end of the instrument coupled to an elongate flexible torque transmitting shaft 14 having a proximal end 16 with proximal and intermediate weld 17 and 18 respectively located proximal to distal end 19 and fixedly coupled scissor blade assembly 20. Handle assembly 12 is of a general type that includes a handle body 22 having a proximal end 24 and a distal end 26. Handle body 22 includes first and second projections 28 and 30 that are spaced apart and extend from the proximal end 24 to the distal end 26. Located at the proximal end 24 of handle body 22 there is an integrally formed thumb ring 32. Positioned on handle body 22 between proximal end 24 and distal end 26 is handle slide 34. Handle slide 34 is configured to surround projections 28 and 30 and partially extend between the projections such that slide 34 is slidable in a longitudinal direction distally and proximally on the projections. Extending from opposite sides of slide 34 are integrally formed finger rings 36 and 38. Centrally located on slide 34 is securing member 40 which typically takes the form of a set screw. Cap member 42 is positioned at the distal end of handle body 22 and couples the proximal end 16 of shaft 14 to handle assembly 12. Actuation member 50 is shown in FIG. 2 positioned within the lumen of shaft 14 extending from proximal end 16 to distal end 19. The proximal end 52 of actuation member 50 is coupled to slide 34 via securing member 40 while the distal end 54 is coupled to blade assembly 20.

Turning now to FIGS. 3A, 3B, 4A and 4B which illustrate an enlarged view of the distal portion of scissor instrument 10, blade assembly 20 is shown in more detail. Blade assembly 20 includes a tubular clevis 60 which is fixedly coupled to shaft distal end 19 at weld 61 located at the clevis proximal end 62. Clevis 60 has a distal end 64 and spaced apart clevis arms 66 and 68. Disposed between clevis arms 66 and 68 is a first scissor blade 70 having a distal end 72, a proximal end 74 and an elongate slot 76 adjacent proximal end 74. A second scissor blade 80 having a distal end 82, a proximal end 84 and an elongate slot 86 adjacent proximal end 84 is also disposed between clevis arms 66 and 68. First and second scissor blades 70 and 80 are pivotally coupled to clevis 60 at distal end 64 through pivot rivet 88.

Figure 3A:
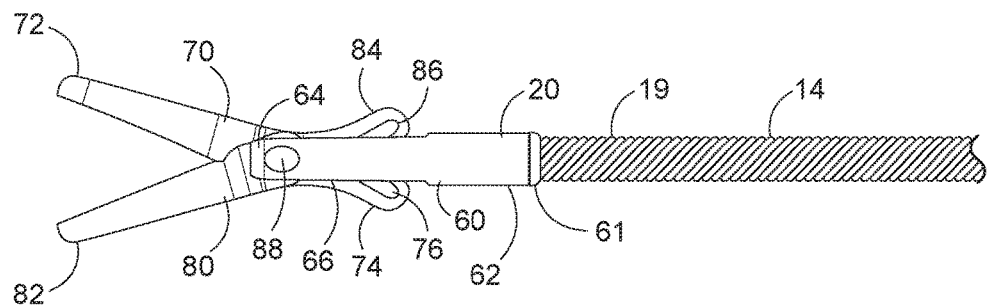
FIG. 3A is an enlarged partial view of the distal end of the flexible endoscopic scissor instrument shown in FIG. 1.
Figure 3B:
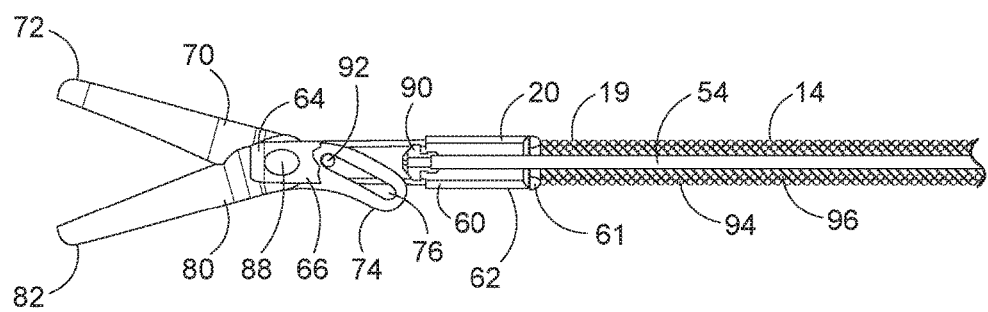
FIG. 3B is a partially sectioned view of the distal end of the flexible endoscopic scissor instrument shown in FIG. 3A.
Figure 4A:
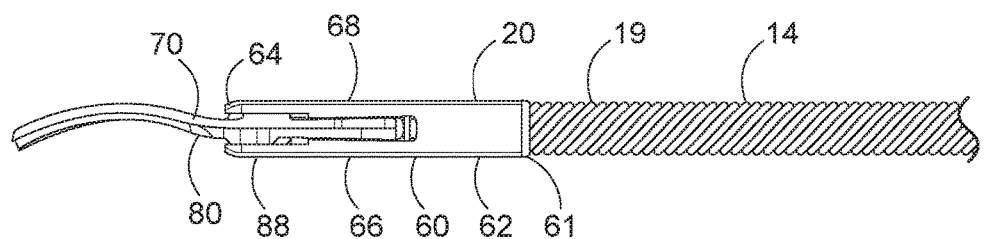
FIG. 4A is an enlarged partial top view of the distal end of the flexible endoscopic scissor instrument shown in FIG. 1.
Figure 4B:
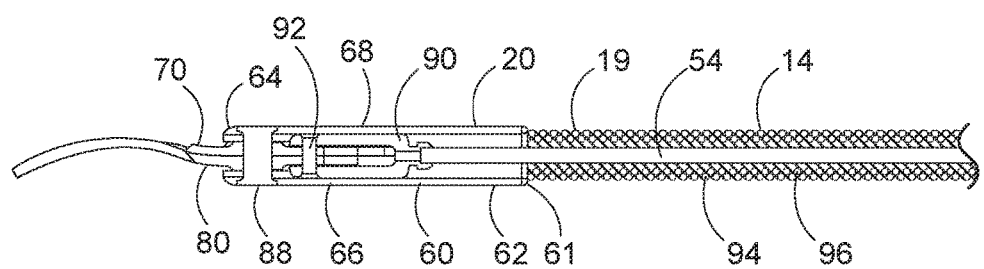
FIG. 4B is a partially sectioned view of the distal end of the flexible endoscopic scissor instrument shown in FIG. 4A.

The partially sectioned view of FIGS. 3B and 4B reveal an internal clevis 90 which is fixedly coupled to distal end 54 of actuation member 50. Clevis pin 92 extends through slots 76 and 86 of scissor blades 70 and 80 to couple the blades to actuation member 50. While scissor blades 70 and 80 are shown in an open configuration and have a generally curved shape, other shapes are contemplated. In the open configuration, the internal clevis pin 92 is positioned at the most distal position possible relative to slots 76 and 86. Hollow torque transmitting shaft 14 is shown in cross section depicting the arrangement of hollow cable 94 and inner coil 96 which are secured together at weld 61.

The hollow cable 94 and the inner coil 96 can be coaxially arranged. Although FIG. 3B depicts the inner coil 96 being positioned in the hollow cable 94, in some embodiments, the hollow cable 94 can be positioned in the coil 96.

The hollow cable 94 can be secured to the inner coil 96 by one or more welds 17, 18, 61, e.g., one weld, two welds, three welds, or more. If the cable 94 is formed from multiple cables, the one or more welds can prevent the cable 94 from unraveling. It may be desirable to include less than or equal to three welds to maximize the flexibility of the shaft 14. In certain aspects, the hollow cable 94 and the inner coil 96 can be secured together by longitudinally spaced apart welds. The one or more welds can be circumferential welds around the shaft 14.

As shown in FIG. 1, the hollow cable 94 can be secured to the inner coil 96 by a first weld 16 positioned at a proximal portion of the shaft 14. In certain aspects, the hollow cable 94 can be secured to the inner coil 96 by a second weld 61 positioned at a distal portion of the shaft 14. The first and second welds 16, 61 can be spaced apart by at least a majority of a length of the shaft 14, or substantially the entire length of the shaft. In certain aspects, the hollow cable 94 can be secured to the inner coil 96 by a third weld 17 positioned closer to the first weld 16 than the second weld 61.

Figure 5:
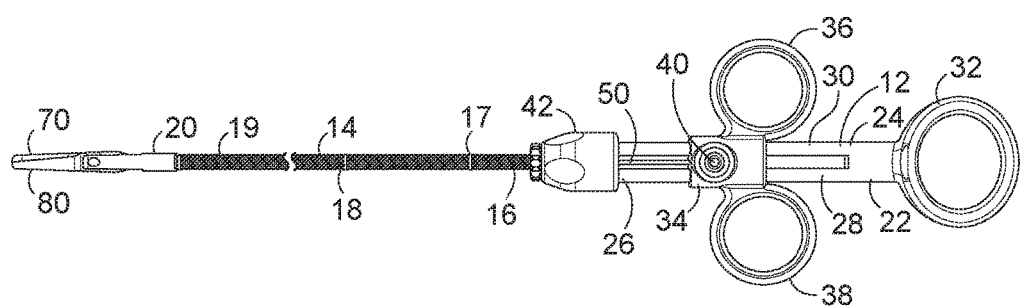
FIG. 5 is a view of a flexible endoscopic scissor instrument with the scissor blades in a closed configuration according to an embodiment of the present disclosure.
Figure 6:
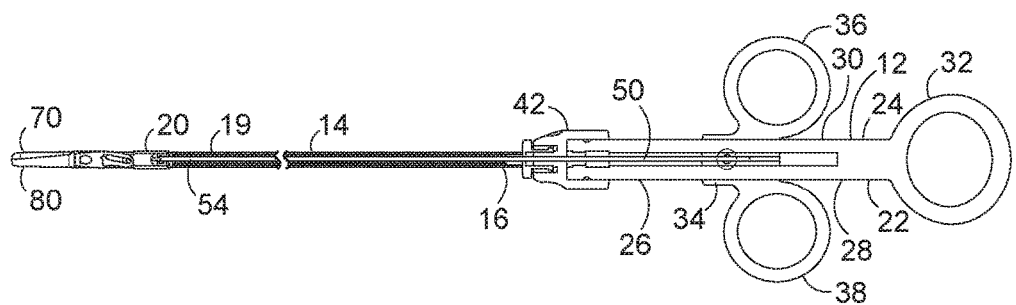
FIG. 6 is a partially sectioned view of the flexible endoscopic scissor instrument shown in FIG. 5.
Figure 7:
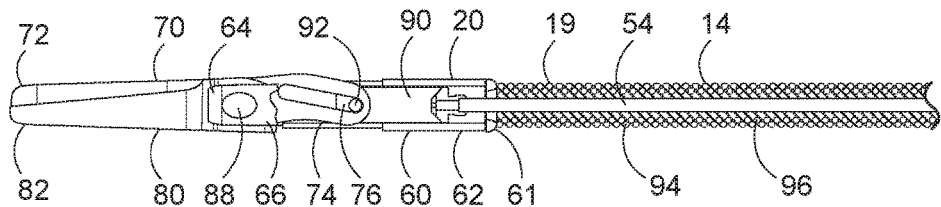
FIG. 7 is an enlarged partially sectioned view of the distal end of the flexible endoscopic scissor instrument shown in FIG. 5.

When scissor blades 70 and 80 are in the open configuration, instrument 10 may be operated to close the scissor blades by moving slide 34 of handle assembly 12 in a proximal direction relative to handle body 22. During this motion, slide 34 which is coupled to actuation member 50 causes the actuation member move proximally relative to shaft member 14. Within scissor blade assembly 20, internal clevis pin 92 is moved proximally along slots 76 and 86 such that scissor blades 70 and 80 pivot about pivot pin 88 to thereby move to the closed configuration as shown in FIGS. 5, 6 and 7. Conversely, to open the scissor blades from the closed configuration, instrument 10 may be operated by moving slide 34 distally to subsequently cause scissor blades 70 and 80 to pivot to the open configuration.

With reference to FIGS. 8-11, another illustrative embodiment of a surgical tool is shown. The scissor instrument 110 resembles or is identical to the scissor instrument 10 discussed above in many respects. Accordingly, numerals used to identify features of the scissor instrument 10 are incremented by a factor of one hundred (100) to identify like features of the scissor instrument 110. This numbering convention generally applies to the remainder of the figures. Any component or step disclosed in any embodiment in this specification can be used in other embodiments.

Figure 8:
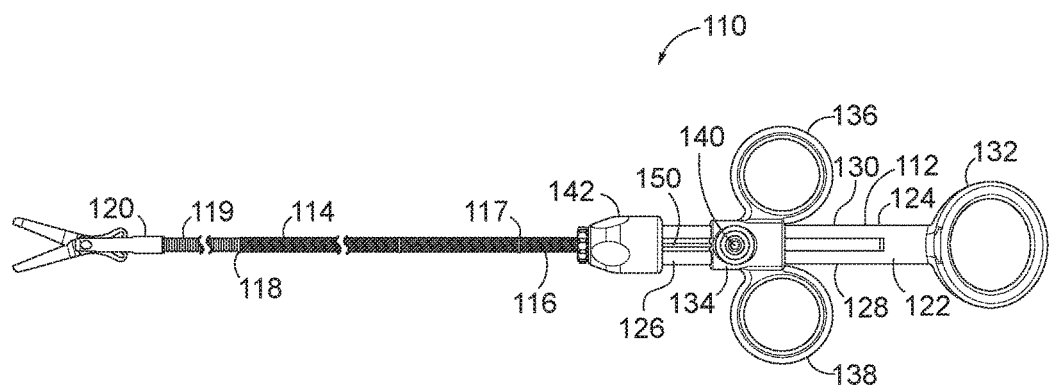
FIG. 8 is a view of a flexible endoscopic scissor instrument with the scissor blades in an open configuration according to another embodiment of the present disclosure.
Figure 9:
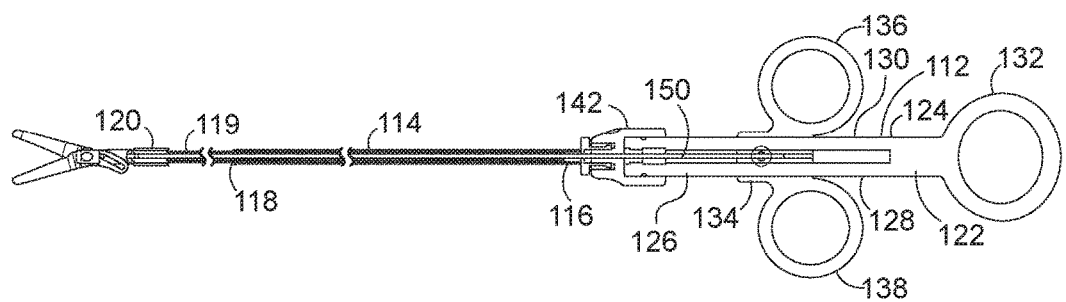
FIG. 9 is a partially sectioned view of the flexible endoscopic scissor instrument shown in FIG. 8

As illustrated in FIG. 8, scissor instrument 110 includes a handle assembly 112 at the proximal end of the instrument coupled to an elongate flexible torque transmitting shaft 114 having a proximal end 116 with proximal and intermediate weld 117 and 118 respectively located proximal to distal end 119 and fixedly coupled scissor blade assembly 120. Handle assembly 112 is of a general type that includes a handle body 122 having a proximal end 124 and a distal end 126. Handle body 122 includes first and second projections 128 and 130 that are spaced apart and extend from the proximal end 124 to the distal end 126. Located at the proximal end 124 of handle body 122 there is an integrally formed thumb ring 132. Positioned on handle body 122 between proximal end 124 and distal end 126 is handle slide 134. Handle slide 134 is configured to surround projections 128 and 130 and partially extend between the projections such that slide 134 is slidable in a longitudinal direction distally and proximally on the projections. Extending from opposite sides of slide 134 are integrally formed finger rings 136 and 138. Centrally located on slide 134 is securing member 140 which typically takes the form of a set screw. Cap member 142 is positioned at the distal end of handle body 122 and couples the proximal end 116 of shaft 114 to handle assembly 112. Actuation member 150 is shown in FIG. 9 positioned within the lumen of shaft 114 extending from proximal end 116 to distal end 119. The proximal end 152 of actuation member 150 is coupled to slide 134 via securing member 140 while the distal end 154 is coupled to blade assembly 120.

Figure 10:
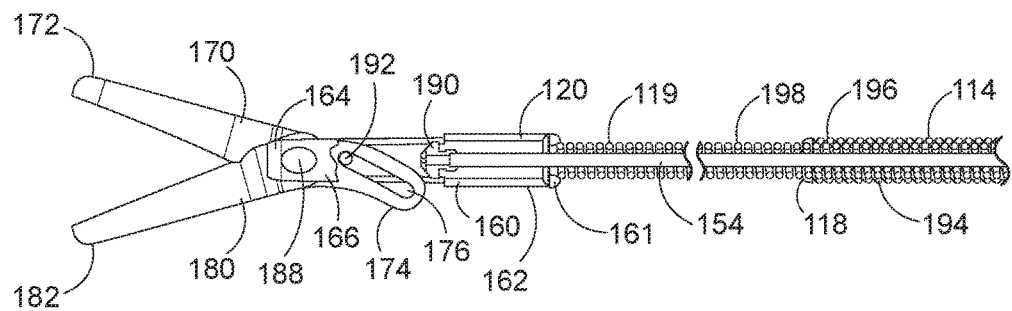
FIG. 10 is an enlarged partially sectioned view of the distal end of the flexible endoscopic scissor instrument shown in FIG. 8.
Figure 11:
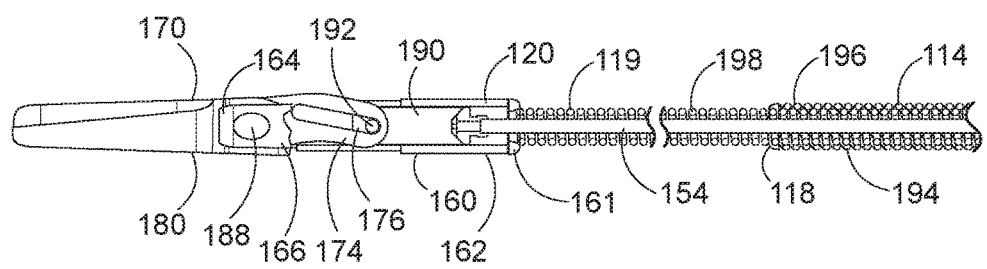
FIG. 11 is an enlarged partially sectioned view of the distal end of the flexible endoscopic scissor instrument of FIG. 8 shown in closed configuration.

Turning now to FIGS. 10 and 11 which illustrate an enlarged view of the distal portion of scissor instrument 110, blade assembly 120 is shown in more detail. Blade assembly 120 includes a tubular clevis 160 which is fixedly coupled to shaft distal end 119 at weld 161 located at the clevis proximal end 162. Clevis 160 has a distal end 164 and spaced apart clevis arms 166 and 168. Disposed between clevis arms 166 and 168 is a first scissor blade 170 having a distal end 172, a proximal end 174 and an elongate slot 176 adjacent proximal end 174. A second scissor blade 180 having a distal end 182, a proximal end 184 and an elongate slot 186 adjacent proximal end 184 is also disposed between clevis arms 166 and 168. First and second scissor blades 170 and 180 are pivotally coupled to clevis 160 at distal end 164 through pivot rivet 188.

The partially sectioned view of FIGS. 10 and 11 reveal an internal clevis 190 which is fixedly coupled to distal end 154 of actuation member 150. Clevis pin 192 extends through slots 176 and 186 of scissor blades 170 and 180 to couple the blades to actuation member 150. While scissor blades 170 and 180 are shown in an open configuration and have a generally curved shape, other shapes are contemplated. In the open configuration, the internal clevis pin 192 is positioned at the most distal position possible relative to slots 176 and 186. Hollow torque transmitting shaft 114 is shown in cross section depicting the arrangement of hollow cable 194 and inner coil 196 which are secured together at weld 118.

As shown in FIG. 10, the distal portion 198 of the inner coil 196 can extend beyond the distal end of the hollow cable 194. This arrangement provides greater flexibility at a distal portion of the shaft 114.

Although certain embodiments have been described herein with respect to scissors, the surgical tools described herein can be graspers, dissectors, needle drivers, suction tools, electrocautery tools, or otherwise.

As used herein, the relative terms "proximal" and "distal" shall be defined from the perspective of the surgical tool. Thus, proximal refers to the direction of the handle and distal refers to the direction of the end effector.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments.

Although certain embodiments and examples have been described herein, it will be understood by those skilled in the art that many aspects of the surgical instruments shown and described in the present disclosure may be differently combined and/or modified to form still further embodiments or acceptable examples. A wide variety of designs and approaches are possible. No feature, structure, or step disclosed herein is essential or indispensable. It will be understood by those skilled in the art that numerous modifications and improvements may be made to the embodiments of the disclosure described herein without departing from the spirit and scope thereof.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. It is intended, therefore, that the specification and examples be considered as illustrative only, with a true scope and spirit being indicated by the claims and their full scope of equivalents.

Any methods disclosed herein need not be performed in the order recited. The methods disclosed herein include certain actions taken by a practitioner; however, they can also include any third-party instruction of those actions, either expressly or by implication. For example, actions such as "rotating a proximal end of the shaft member to rotate the end effector" include "instructing rotation of a proximal end of the shaft member to rotate the end effector."

The ranges disclosed herein also encompass any and all overlap, sub-ranges, and combinations thereof. Language such as "up to," "at least," "greater than," "less than," "between" and the like includes the number recited. Numbers preceded by a term such as "about" or "approximately" include the recited numbers. For example, "about 3 mm" includes "3 mm."

That which is claimed is:

1. A flexible endoscopic scissor instrument for use through the working channel of a flexible endoscope, the instrument comprising:
   an elongate flexible hollow torque transmitting shaft member having proximal and distal ends and a lumen extending through said shaft member, wherein said shaft member includes an elongate hollow cable member having proximal and distal ends and an elongate coil member having proximal and distal ends, said cable member and said coil member being in coaxial arrangement,
   an elongate actuation member having proximal and distal ends, said actuation member being slidably positioned within the lumen of said shaft member,
   a handle member having a body portion and a slidable portion positioned at the proximal end of said shaft member, wherein said body portion is coupled to said proximal end of said shaft member in a longitudinally fixed configuration and said slidable portion is coupled to the proximal end of said actuation member, and
   a blade assembly positioned at the distal end of said shaft member, the blade assembly including a pair of pivotally connected scissor blades at the distal end of the blade assembly, each of said scissor blades having a proximal end and a distal end, wherein the proximal ends of said blades are coupled to the distal end of said actuation member such that longitudinal movement of said actuation member causes said scissor blades to open or close, said blade assembly being fixedly joined to the distal end of said shaft member such that rotation of the proximal end of said shaft member causes the blade assembly to rotate.

2. An endoscopic scissor instrument according to claim 1 wherein said coil member is positioned within said hollow cable member.

3. An endoscopic scissor instrument according to claim 1 wherein said coil member is welded to said hollow cable member.

4. An endoscopic scissor instrument according to claim 1 wherein said coil member is welded to said hollow cable member in at least two longitudinally spaced apart locations.

5. An endoscopic scissor instrument according to claim 1 wherein said actuation member takes the form of a flexible wire.

6. An endoscopic scissor instrument according to claim 1 wherein said actuation member takes the form of a flexible cable.

7. A flexible endoscopic scissor instrument for use through the working channel of a flexible endoscope comprising:
   an elongate flexible hollow torque transmitting shaft member having proximal and distal ends and a lumen extending through said shaft member, wherein said shaft member includes an elongate hollow cable member having proximal and distal ends and an elongate coil member having proximal and distal ends, said cable member and said coil member being in coaxial arrangement and the distal end of said coil member extends distal to the distal end of said cable member,
   an elongate actuation member having proximal and distal ends, said actuation member being slidably positioned within the lumen of said shaft member,
   a handle member having a body portion and a slidable portion positioned at the proximal end of said shaft member, wherein said body portion is coupled to said proximal shaft member in a longitudinally fixed configuration and said slidable portion is coupled to the proximal end of said actuation member, and
   a blade assembly positioned at the distal end of said shaft member including a pair of pivotally connected scissor blades at the distal end of the scissors, said scissor blades each having a proximal end and a distal end wherein the proximal end of said blades are coupled to the distal end of said actuation member such that longitudinal movement of said actuation member causes said scissor blades to open or close, said blade assembly being fixedly joined to said shaft member distal end such that rotation of the proximal end of said shaft member causes the blade assembly to rotate.

8. An endoscopic scissor instrument according to claim 7, wherein said coil member is positioned within said hollow cable member.

9. An endoscopic scissor instrument according to claim 7, wherein said coil member is welded to said hollow cable member.

10. An endoscopic scissor instrument according to claim 7, wherein said coil member is welded to said hollow cable member in at least two longitudinally spaced apart locations.

11. An endoscopic scissor instrument according to claim 7, wherein said actuation member takes the form of a flexible wire.

12. An endoscopic scissor instrument according to claim 7, wherein said actuation member takes the form of a flexible cable.

13. A flexible endoscopic surgical instrument:
   an elongate, flexible shaft member having a proximal portion, a distal portion, and a lumen extending therethrough, the shaft member configured for delivery through a working channel of an endoscope, the shaft member comprising:
     an elongate cable member having a proximal portion and a distal portion, and
     an elongate coil member having a proximal portion and a distal portion, the cable member and the coil member being in coaxial arrangement;
   an elongate actuation member having a proximal portion and a distal portion, the actuation member being slidably positioned within the shaft member;
   a handle member comprising a body portion and a slidable portion, the body portion being coupled to the proximal portion of the shaft member in a longitudinally fixed configuration, the slidable portion being coupled to the proximal portion of the actuation member; and
   an end effector coupled to the distal portion of the actuation member such that longitudinal movement of the actuation member actuates the end effector,
   wherein rotation of the proximal portion of the shaft member is configured to rotate the end effector.

14. The flexible endoscopic surgical instrument of claim 13, wherein a diameter of the shaft member is less than or equal to about 3.2 mm.

15. The flexible endoscopic surgical instrument of claim 13, wherein the cable member is secured to the coil member by a number of welds.

16. The flexible endoscopic surgical instrument of claim 15, wherein the number of welds comprises two longitudinally spaced apart welds.

17. The flexible endoscopic surgical instrument of claim 13, wherein the distal portion of the coil member extends distal to the distal end of the cable member.

18. The flexible endoscopic surgical instrument of claim 13, wherein the elongate coil member is positioned in the elongate cable member.

* * * * *